United States Patent [19]
Hishii et al.

[11] 4,377,944
[45] Mar. 29, 1983

[54] INTEGRATED GAS SENSITIVE UNIT COMPRISING A GAS SENSITIVE SEMICONDUCTOR ELEMENT AND A RESISTOR FOR GAS CONCENTRATION MEASUREMENT

[75] Inventors: Toshiyasu Hishii; Tokuo Takeuchi; Nobuaki Shohata; Toshio Takaba; Koichi Saito, all of Tokyo, Japan

[73] Assignee: Nippon Electric Co., Ltd., Tokyo, Japan

[21] Appl. No.: 220,712

[22] Filed: Dec. 29, 1980

[30] Foreign Application Priority Data

Dec. 27, 1979 [JP] Japan ............................... 54-170725
Dec. 27, 1979 [JP] Japan ............................... 54-170726

[51] Int. Cl.³ ............................................ G01N 27/12
[52] U.S. Cl. ........................................ 73/23; 338/34
[58] Field of Search ................... 73/23, 27 R; 338/34; 422/98

[56] References Cited
U.S. PATENT DOCUMENTS 3,578,409  5/1971  Silverman et al. ............... 73/27 R
3,901,067  8/1975  Boardman, Jr. et al. ............ 73/23
4,007,435  2/1977  Tien ............................... 338/34

*Primary Examiner*—Stephen A. Kreitman
*Attorney, Agent, or Firm*—Laff, Whitesel, Conte & Saret

[57] ABSTRACT

For use in a gas sensor, an integrated gas sensitive unit comprises, on a single principal surface, a gas sensitive semiconductor element and a first resistor member connected to the element in series for deriving an electrical signal from the element. Both of the element and the first resistor member may be formed by the thick-film integration technique. A heating wire may be attached to the back surface opposite to the principal surface. A combination of secnd and third resistor members may be electrically connected to the series connection in parallel with the second and the third resistor members brought into electrical contact with the element and the first resistor member, respectively, to form a bridge circuit. The combination may be formed on the principal surface together with the series connection or separated from the series connection. Preferably, the first or the second resistor member has the same temperature dependency as the element when the heating wire is attached to the bridge circuit.

7 Claims, 9 Drawing Figures

INTEGRATED GAS SENSITIVE UNIT COMPRISING A GAS SENSITIVE SEMICONDUCTOR ELEMENT AND A RESISTOR FOR GAS CONCENTRATION MEASUREMENT

BACKGROUND OF THE INVENTION

This invention relates to a gas sensitive unit for use in a gas sensor in detecting a gas, such as methane, ethane, propane, normal butane, isobutane, a mixture thereof, carbon monoxide, or town gas. The gas sensor indicates the concentration of the gas in the surrounding atmosphere and alarms leakage of such a gas.

A conventional gas sensitive unit comprises a gas sensitive semiconductor element, which has an electrical conductivity between $10^3$ and $10^{-10}$ mho/cm at normal temperature. Typical semiconductor material is stannic oxide ($SnO_2$) and gamma-ferric oxide ($\gamma$-$Fe_2O_3$). The conductivity generally grows greater with the ambient temperature and an increase in the concentration of the gas in the surrounding atmosphere. As described in U.S. Pat. No. 3,695,848 issued to Naoyoshi Taguchi, the semiconductor material has a substantially linear characteristic versus the gas concentration when heated to about $150°-250°$ C. The gas sensitive unit has therefore been manufactured as a combination of the semiconductor element and a heating wire.

For use as the gas sensor, it is necessary to combine an electrical circuit with the gas sensitive element. Inasmuch as the gas sensitive unit has been manufactured as a combination, it has not been tried to manufacture the gas sensor as an integrated circuit. As a result, a gas sensor has been bulky. It has been difficult to manufacture the gas sensor in mass production.

When a bridge circuit is used as the electrical circuit, the combination of the gas sensitive semiconductor element and the heating wire has made it necessary to manually adjust the bridge. As a result of the troublesome manual adjustment, the gas sensor has been defective in the sensitivity and the stability.

SUMMARY OF THE INVENTION

It is an object of this invention to provide a gas sensitive unit, which is compact.

It is another object of this invention to provide a gas sensitive unit of the type described, which is manufactured in mass production according to the manufacture technique of integrated circuits.

It is a further object of this invention to provide a gas sensitive unit of the type described, which need not any manual adjustment and has high sensitivity and high stability.

According to this invention there is provided a gas sensitive unit for use in detecting a gas to indicate presence of the gas. The unit comprises a first substrate of an electrical insulator having a first flat principal surface, a first conductor pattern on the first principal surface, a second conductor pattern on the first principal surface with a space left between the first and the second conductor patterns, a third conductor pattern on the first principal surface in the space between the first and the second conductor patterns, and an element of a gas sensitive semiconductor electrically connected between the first and the third conductor patterns. The gas sensitive semiconductor has an electrical conductivity which is variable when the gas sensitive semiconductor is brought into contact with the gas. The unit further comprises a first resistor member electrically connected between the third and the second conductor patterns and thereby combined with the semiconductor element on the first principal surface. The first resistor member is insensitive to the gas and is substantially non-exothermal when electrically energized.

DESCRIPTION OF THE PREFERRED EMBODIMENTS

Figure 1:
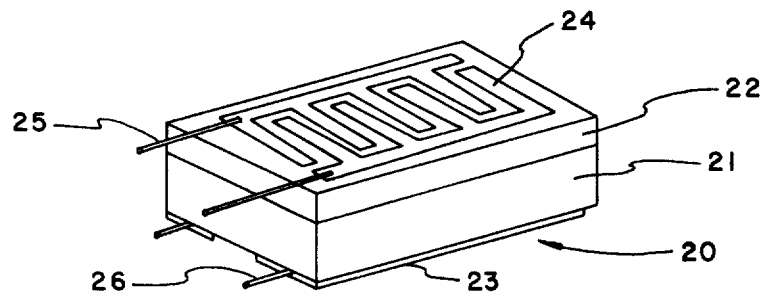
FIG. 1 is a perspective view of a conventional gas sensitive unit.

Referring to FIG. 1, a conventional gas sensitive unit 20 is for use in a gas sensor and comprises a substrate 21 of an electrical insulator having a front surface and a back surface opposite to the front surface. A gas sensitive film 22 of a semiconductor, such as gamma-ferric oxide, is attached to the front surface of the substrate 21. Such a semiconductor is sensitive to a reducing gas and has an electrical conductivity substantially linearly variable or increasing when exposed to the gas at a raised temperature as described in the preamble of the instant specification. A heater 23 of platinum is attached to the back surface of the substrate 21 to heat the gas sensitive film 22 to the raised temperature. A pair of interdigital electrodes 24 are arranged on the gas sensitive film 22. First and second pairs of lead wires 25 and 26 are connected to the electrodes 24 and the heater 23, respectively. Thus, the gas sensitive film 22 is combined with the heater 23 to form the gas sensitive unit 20.

Figure 2:
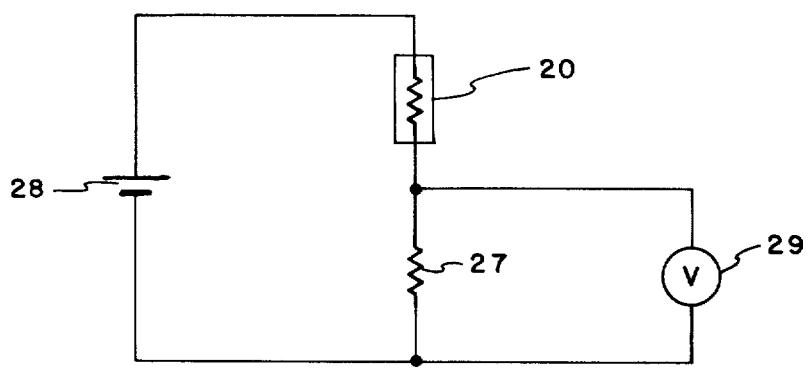
FIG. 2 shows a circuit diagram of a gas sensor comprising either the conventional gas sensitive unit or a gas sensitive unit according to this invention.

Referring to FIG. 2, a gas sensor comprises the gas sensitive unit 20 illustrated in FIG. 1 and an electrical circuit connected thereto. From FIG. 2, the heater 23 is omitted. The illustrated electrical circuit comprises a resistor 27 connected to the gas sensitive unit 20 in series. The resistor 27 is manufactured separately from the gas sensitive unit 20 and thereafter assembled with the same. Therefore, the gas sensor circuit is bulky. The resistor 27 itself is substantially non-exothermal even when an electrical current flows through the resistor 27. A d.c. power source 28 is connected across the series connection of the gas sensitive unit 20 and the resistor 27 while a voltmeter 29, across the resistor 27.

In FIG. 2, the voltmeter 29 indicates a prescribed voltage insofar as there is no gas contact in the atmosphere surrounding the gas sensitive unit 20. On the other hand, indication of the voltmeter 29 varies from the prescribed voltage when the gas to be detected is present in the surrounding atmosphere.

Figure 3:
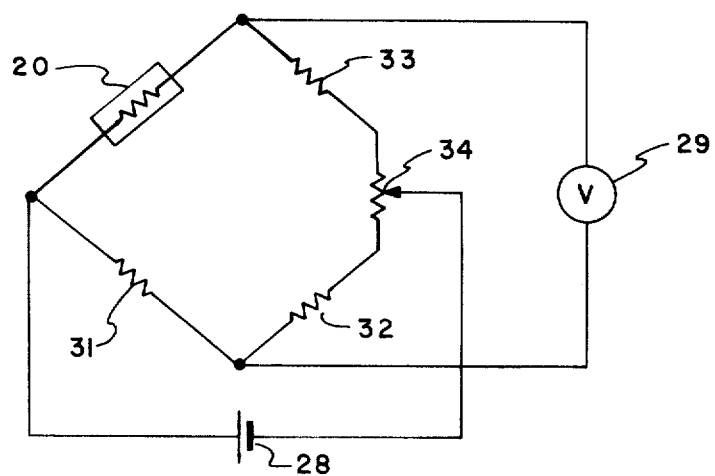
FIG. 3 is a circuit diagram of a conventional gas sensor comprising an electrical circuit of a bridge type.

Referring to FIG. 3, a conventional gas sensor comprises an electrical circuit of a bridge type. The gas sensitive unit 20 illustrated in FIG. 1 is comprised by one of the bridge arms. First, second, and third fixed resistors 31, 32, and 33, and a single variable resistor 34 are connected to form the remaining bridge arms. The variable resistor 34 is connected between the second and the third fixed resistors 32 and 33 and has a manually adjustable terminal. A d.c. power source 28 similar to that of FIG. 2 is connected between the manually adjustable terminal and a first point of connection between the gas sensitive unit 20 and the first fixed resistor 31. A voltmeter 29 is connected between a second point of connection between the first and the second fixed resistors 31 and 32 and a third point of connection between the third fixed resistor 33 and the gas sensitive unit 20.

In FIG. 3, the gas sensor should be put in a state of equilibrium by manually adjusting the variable resistor 34 at the rasied temperature. When brought into contact with the gas, the electrical conductivity of the gas sensitive unit 20 varies to develop an unbalance voltage between the second and the third points of connection. The voltmeter 29 detects the unbalance voltage to indicate presence of the gas.

The gas sensor is manufactured by individually preparing the gas sensitive unit 20 and the remaining resistors 31–34 and by combining the former with the latter. Therefore, the gas sensor has the defects described in the preamble of the instant specification. In addition, manual adjustment should be carried out with the gas sensitive semiconductor 22 (FIG. 1) heated to the high temperature.

Figure 4:
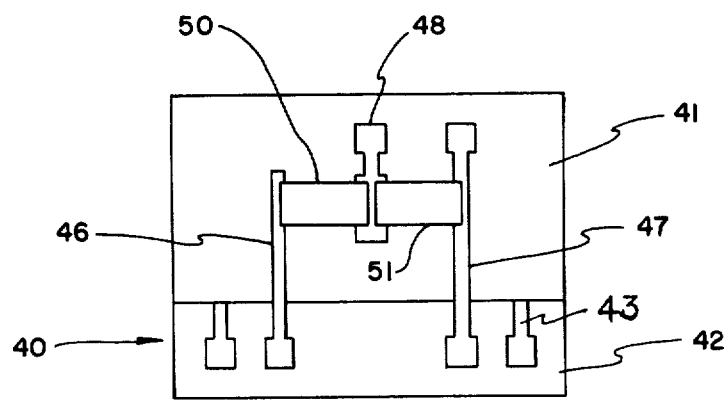
FIG. 4 is a top view of a gas sensitive unit according to a first embodiment of this invention.

Referring to FIG. 4, a gas sensitive circuit unit 40 according to a first embodiment of this invention is electrically equivalent to that portion of the gas sensor of FIG. 2 from which the d.c. power source 28 and the voltmeter 29 are removed. The gas sensitive circuit unit 40 comprises a first substrate 41 of an electrical insulator, such as alumina ceramic. The first substrate 41 has a front or first principal surface and a back surface opposite to the front surface. The first substrate 41 is superposed on a second substrate 42, such as alumina ceramic. The second substrate 42 has a second principal surface attached to the back surface with an area of the second principal surface left uncovered with the first substrate 41. In the example being illustrated, the first substrate 41 is 40 mm×70 mm×50 microns while the second substrate 42 is 50 mm×70 mm×0.5 mm.

Figure 5:
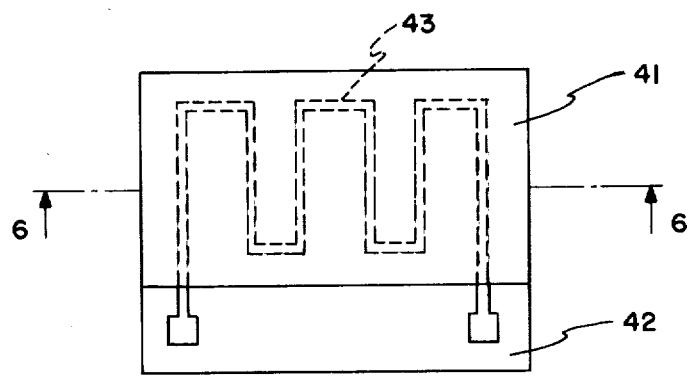
FIG. 5 shows, with parts removed, a top view of the gas sensitive unit depicted in FIG. 4.
Figure 6:
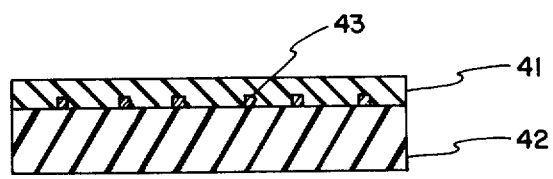
FIG. 6 is a sectional view of the gas sensitive unit portion illustrated in FIG. 5, the section being taken along a line 6—6 indicated in FIG. 5.

Temporarily referring to FIGS. 5 and 6 in addition to FIG. 3, the circuit unit 40 comprises a heating wire 43 on the second principal surface. Preferably, the heating wire 43 is embedded in the back surface of the first substrate 41. The heating wire 43 is of a heatable material, for example, platinum, which is exothermal when electrically energized. The heating wire 43 has a pair of ends on the uncovered area of the second principal surface and a meandering portion connected to the end pair and covered with the first substrate 41. The heating wire 43 may be 25 microns thick.

Turning back to FIG. 4, a first conductor pattern 46 has a first conductor portion on the first principal surface and a first extension on the second principal surface. Likewise, a second conductor pattern 47 has a second conductor portion and a second extension. The first and the second extensions are for connection to the d.c. power source 28 as shown in FIG. 2. The first and the second conductor patterns 46 and 47 are substantially parallel to each other and leave a space therebetween. Each of the first and second conductor patterns 46 and 47 may be of silver-palladium alloy and 25 microns thick.

The illustrated circuit unit 40 further comprises a third conductor pattern 48 on the first principal surface in the space between the first and the second conductor patterns 46 and 47. The third conductor pattern 48 is substantially parallel to each of the first and the second conductor patterns 46 and 47. An element or layer 50 of a gas sensitive semiconductor, such as stannic oxide, is electrically connected between the first and the third conductor patterns 46 and 48. The layer 50 is formed by printing a paste of stannic oxide, ethyl cellulose, and betaterpineol. The semiconductor element or layer 50 has a gas sensitive property such that the electrical conductivity is variable when the element 50 is brought into contact with the gas.

A first resistor 51 is formed on the first principal surface between the third and the first conductor patterns 48 and 46 to be electrically connected to them. The first resistor 51 is substantially non-exothermal even when electrically energized and is insensitive to the gas. The illustrated first resistor 51 is formed by a layer of ruthenium oxide, 25 microns thick, and has a resistance of several hundreds of kiloohms. The resistor 51 is printed to be attached to the first substrate 41. Thus, the gas sensitive semiconductor element 50 is combined with the non-exothermal resistor 51 to form an integrated circuit unit 40.

A d.c. power source 28 and a voltmeter 29 are connected between the first and the second conductor patterns 46 and 47 and between the third and the second conductor patterns 48 and 46, as shown in FIG. 2.

When high sensitivity and high stability are not necessary in a gas sensitive unit 40, the heating wire 43 and the second substrate 42 may be omitted from the circuit unit 40.

Figure 7:
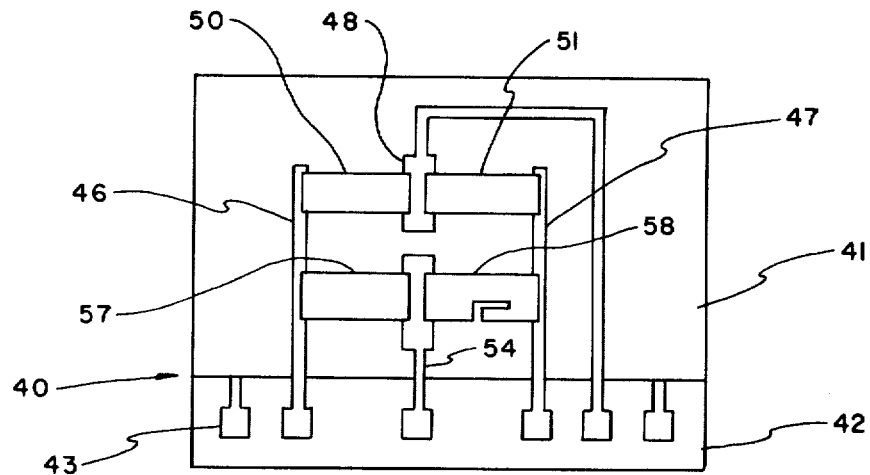
FIG. 7 is a top view of a gas sensitive unit according to a second embodiment of this invention.

Referring to FIG. 7, a gas sensitive unit according to a second embodiment of this invention comprises similar parts designated by like reference numerals. In FIG. 7, the third conductor pattern 48 has a third conductor portion substantially parallel to the first and the second conductor patterns 46 and 47 and a third extension attached to the third conductor portion and extended onto the second principal surface. A fourth conductor pattern 54 is laid between the first and the second conductor patterns 46 and 47 and is spaced from the third conductor pattern 48. The fourth conductor pattern 54 has a fourth conductor portion on the first principal surface and a fourth extension on the second principal surface. Thus, all ends of the heating wire 43 and the first through the fourth extensions are placed on the second principal surface.

Although designated by the same reference numeral 51, the first resistor will be referred to as a first resistor member hereinafter.

In FIG. 7, the circuit unit 40 further comprises a second resistor member 57 between the first and the fourth conductor patterns 46 and 54 and a third resistor member 58 between the fourth and the second conductor patterns 54 and 47. The first conductor pattern 46 is electrically connected to the fourth conductor pattern 54 through the second resistor member 57 while the fourth conductor pattern 54, to the second conductor pattern 47 through the third resistor member 58. Both of the second and third resistor members 57 and 58 may be of ruthenium oxide and 25 microns thick and have the resistances of several hundred kiloohms. They are formed by the use of a conventional thick-film integration technique. The first and the second resistor members 57 and 58 are insensitive to the gas exemplified in the preamble of the instant specification and are non-exothermal even when electrically energized, as is the case with the first resistor member 51.

As will readily be understood from FIG. 7, a bridge circuit is formed by a combination of the semiconductor element or layer 50 and the first through third resistor members 51, 57, and 58. A d.c. power source 28 and a voltmeter 29 are connected between the first and the second conductor patterns 46 and 47 and between the third and the fourth conductor patterns 48 and 54, respectively, as suggested in FIG. 3. Inasmuch as the first through third resistor members 51, 57, and 58 are arranged on the same principal surface as the semiconductor layer 50, they are kept at a temperature substantially equal to that of the semiconductor element 50 when the bridge circuit is heated by the heating wire 43. The gas sensitive semiconductor element 50 usually has a temperature dependency different from that of each of the second and the third resistor members 57 and 58. The temperature of the circuit unit 40 is not always kept constant but is often dependent on the ambient temperature. Under the circumstances, the bridge circuit may erroneously be changed from a state of equilibrium in spite of no contact of the gas with the semiconductor element 50.

Taking the above into consideration, the first resistor member 51 preferably comprises a layer of stannic oxide having a temperature dependency substantially equal to that of the gas sensitive semiconductor or stannic oxide. The stannic oxide is usually sensitive to the gas. The stannic oxide layer is, therefore, covered with a gas insensitive layer of, for example, epoxy resin to prevent the stannic oxide layer from being exposed to the gas. Alternatively, it is known in the art to obtain stannic oxide insensitive to the gas. Use of such stannic oxide makes the epoxy resin layer unnecessary.

In the example being illustrated, the third resistor member 58 is trimmed by laser trimming or abrasive trimming to adjust or increase its resistance to a desirable value and to put the bridge circuit into the state of equilibrium when the circuit unit 40 is tested. The adjustment of the resistance may be carried out at normal temperature because the first resistor member 51 has the same temperature dependency as the semiconductor element 50. As a result, the third resistor member 58 has a trimmed portion narrower in width than the remaining portion thereof. So that a product of resistances between the semiconductor element 50 and the third resistor member 58 becomes equal to a product of resistances between the first and the second resistor members 51 and 57.

In operation, the heating wire 43 is connected to an electrical power source (not shown) to heat the gas sensitive unit 40. When the semiconductor element 50 is brought into contact with the gas, an unbalance voltage appears between the third and the fourth conductor patterns 48 and 54 and is indicated by the voltmeter.

Figure 8:
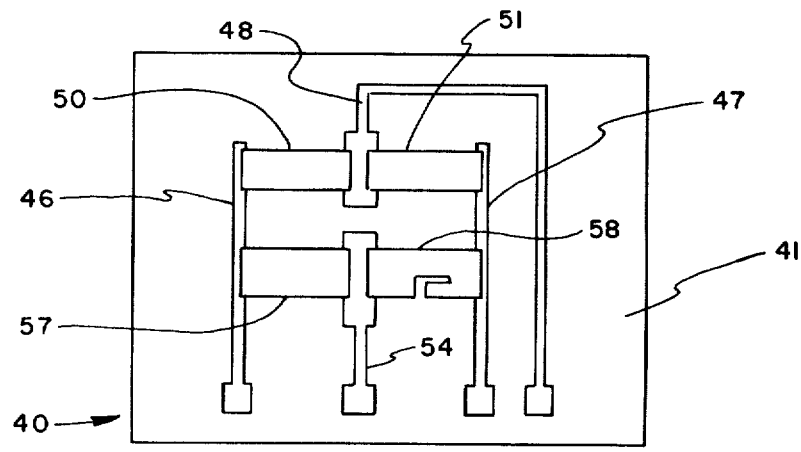
FIG. 8 is a similar view of a gas sensitive unit according to a third embodiment of this invention.

Referring to FIG. 8, a circuit unit 40 according to a third embodiment of this invention is similar to that illustrated with reference to FIG. 7 except that the heating wire 43 and the second substrate 42 are removed from FIG. 8. The first through fourth conductor patterns 46, 47, 48, and 54 are printed on the first principal surface of the first substrate 41 together with the semiconductor element or layer 50 and the first through third resistor members 51, 57, and 58. In FIG. 8, the third resistor member 58 has a trimmed portion narrower in width than the remaining portion thereof. The first through third resistor members 51, 57, and 58 are of ruthenium oxide. As is the case with FIG. 7, the first resistor member 51 may comprise a layer of stannic oxide and a gas insensitive layer of epoxy resin attached to the stannic oxide layer.

The illustrated circuit unit 40 is effective when high sensitivity is not required thereto.

Figure 9:
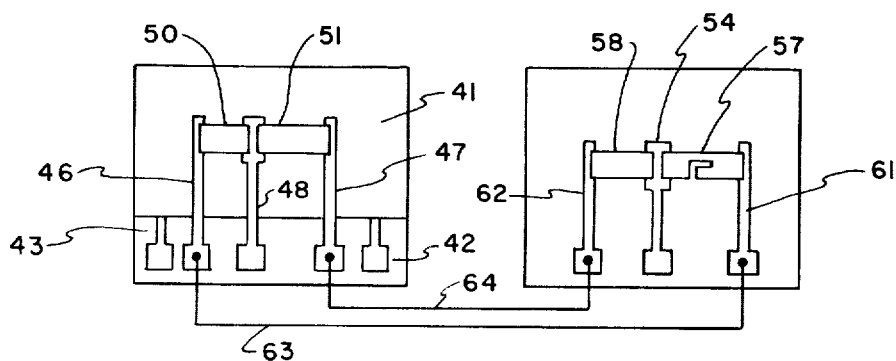
FIG. 9 is a similar view of a gas sensitive unit according to a fourth embodiment.

Referring to FIG. 9, a circuit unit 40 according to a fourth embodiment of this invention comprises similar parts designated by like reference numerals. The left-hand half of FIG. 9 is substantially equivalent to the circuit unit illustrated in FIG. 4 except that the first resistor member 51 comprises a stannic oxide layer and a covering layer of epoxy resin, like in FIG. 7.

In FIG. 9, the circuit 40 further comprises, together with the first and the second substrates 41 and 42 described with reference to FIG. 3, a third substrate of an electrical insulator, such as alumina ceramic, having a third principal surface. On the third principal surface, first and second additional conductors 61 and 62 are placed with a space left therebetween to be electrically connected to the first and the second conductor patterns 46 and 47 through first and second lead wires 63 and 64, respectively. A fourth conductor pattern, which is designated by the same reference numeral 54 as that of FIG. 7, is laid on the third principal surface between the first and the second additional conductors 61 and 62.

Second and third resistor members, which are also designated by the same reference numerals 57 and 58 as those of FIG. 7, are formed by the use of a thick-film integration technique. The second resistor member 57 is brought into electrical contact with the first additional conductor 61 and the fourth conductor pattern 54 while the third resistor member 58, with the second additional conductor 62 and the fourth conductor pattern 54. A d.c. power source 28 and a voltmeter 29 are connected in a manner described with reference to FIG. 7. Thus, the gas sensitive unit forms a bridge circuit, like in FIG. 7 and is, therefore, electrically equivalent to the circuit unit of FIG. 7. The second resistor member 57 is partially trimmed to keep the bridge circuit at the state of equilibrium.

In FIG. 9, the semiconductor element 50 and the first resistor member 51 alone are heated by the heating wire 43 independently of the second and the third resistor members 57 and 58. This means that the first and the second substrates 41 and 42 may be of small size or of low heat capacity, as compared with those illustrated in FIG. 7. Therefore, it is possible with the circuit unit to reduce electrical power consumption in comparison with that of FIG. 7. Inasmuch as the second and the third resistor members 57 and 58 are not heated by the heating wire 43 and are not varied too much in their resistances, it is possible to accomplish temperature compensation at a high precision. Therefore, the circuit unit 40 has high sensitivity and high stability as compared with the circuit units illustrated in FIGS. 7 and 8.

On the description of the embodiments of this invention, it is stated that the semiconductor element 50 and the first through third resistor members 51, 57, and 58 are non-exothermal. The resistors are not endothermal, either.

While this invention has thus far been described in connection with some embodiments thereof, it is now readily possible for those skilled in the art to put this invention in practice in various manners. For example, the second resistor member 57 illustrated in FIG. 7 may comprise a stannic oxide layer and a gas insensitive layer, instead of the first resistor member 51. Alternatively, all of the first through third resistor members 51, 57, and 58 shown in FIG. 7 have the same structure as the first resistor member 51 described with reference to FIG. 7. In FIGS. 7, 8, and 9, at least one of the first through third resistor members and the semiconductor element 50 may be trimmed to control their resistances.

What is claimed is:

1. A gas sensitive unit for use in detecting a gas to indicate presence of said gas, said unit comprising:
   a first substrate of an electrical insulator having a first principal surface;
   a first conductor pattern on said first principal surface;
   a second conductor pattern on said first principal surface with a space left between said first and said second conductor patterns;
   a third conductor pattern on said first principal surface in the space between said first and said second conductor patterns;
   a fourth conductor pattern on said first principal surface intermediate between said first and said second conductor patterns and spaced from said third conductor pattern;
   an element of a gas sensitive semiconductor electrically connected between said first and said third conductor patterns, said gas sensitive semiconductor having an electrical conductivity which has a predetermined temperature dependency and is variable when said gas sensitive semiconductor is brought into contact with said gas;
   a first resistor member electrically connected between said third and said second conductor patterns and thereby combined with said semiconductor element on said first principal surface, said first resistor member being insensitive to said gas and being substantially non-exothermal when electrically energized;
   a second resistor member electrically connected between said first and said fourth conductor patterns; and
   a third resistor member electrically connected between said fourth and said second conductor patterns, said second and said third conductor patterns being insensitive to said gas and being substantially non-exothermal when electrically energized;
   either of said first and said second resistor members comprising a first layer of a material which is the same as said gas sensitive semiconductor and a second layer which is insensitive to said gas and covers said first layer to prevent the same from being exposed to said gas.

2. A gas sensitive unit as claimed in claim 1, said first substrate having a back surface opposite to said first principal surface, wherein said unit comprises:
   a second substrate of an electrical insulator having a second principal surface attached to said back surface with an area of said second principal surface left uncovered with said first substrate; and
   a heating wire of a heatable material placed on said second principal surface and covered with said first substrate with a pair of ends extended on said uncovered area.

3. A gas sensitive unit as claimed in claim 2, wherein said heating wire has a meandering portion electrically connected to said end pair and embedded in said first substrate.

4. A gas sensitive unit as claimed in claims 1, 2, or 3 wherein at least one of said element and said first through third resistor members has a portion narrower in width than the remaining portion thereof.

5. A gas sensitive unit for use in detecting a gas to indicate presence of said gas, said unit comprising:
   a first substrate of an electrical insulator having a first principal surface;
   a first conductor pattern on said first principal surface;
   a second conductor pattern on said first principal surface with a space left between said first and said second conductor patterns;
   a third conductor pattern on said first principal surface in the space between said first and said second conductor patterns;
   an element of a gas sensitive semiconductor electrically connected between said first and said third conductor patterns, said gas sensitive semiconductor having an electrical conductivity which has a predetermined temperature dependency and is variable when said gas sensitive semiconductor is brought into contact with said gas;
   a first resistor member electrically connected between said third and said second conductor patterns and thereby combined with said semiconductor element on said first principal surface;
   a second substrate of an electrical insulator having a second principal surface attached to said back surface with an area of said second principal surface left uncovered with said first substrate;
   a third substrate of an electrical insulator having a third principal surface;
   a first additional conductor on said third principal surface;
   a second additional conductor on said third principal surface with a space left between said first and said second additional conductors;
   a fourth conductor pattern on said third principal surface between said firest and said second additional conductors;
   a second resistor member electrically connected between said first additional conductor and said fourth conductor patterns;
   a third resistor member electrically connected between said second additional conductor and said fourth conductor pattern, said second and said third resistor members being insensitive to said gas and being substantially non-exothermal when electrically energized;
   means for electrically connecting said first conductor pattern to said first additional conductor; and
   means for electrically connecting said second conductor pattern to said second additional conductor;
   said first resistor member comprising a first layer of a material which is the same as said gas sensitive semiconductor and a second layer which is insensitive to said gas and covers said first layer to prevent the same from being exposed to said gas.

6. A gas sensitive unit as claimed in claim 5, further comprising:
   a heating wire of a heatable material placed on said second principal surface and covered with said first substrate, and a pair of end portions extended on said uncovered area.

7. A gas sensitive unit as claimed in claims 5 or 6, wherein at least one of said element and said first through third resistor members has a portion narrower in width than the remaining portion thereof.

* * * * *